(12) United States Patent
Kovac et al.

(10) Patent No.: US 8,166,977 B2
(45) Date of Patent: *May 1, 2012

(54) PELVIC SURGERY DRAPE

(75) Inventors: S. Robert Kovac, Atlanta, GA (US); Robert E. Lund, Eagan, MN (US)

(73) Assignee: AMS Research Corporation, Minnetonka, MN (US)

(*) Notice: Subject to any disclaimer, the term of this patent is extended or adjusted under 35 U.S.C. 154(b) by 109 days.

This patent is subject to a terminal disclaimer.

(21) Appl. No.: 11/986,556

(22) Filed: Nov. 21, 2007

(65) Prior Publication Data
US 2008/0127985 A1 Jun. 5, 2008

Related U.S. Application Data

(63) Continuation of application No. 09/749,254, filed on Dec. 27, 2000, now Pat. No. 7,299,803.

(60) Provisional application No. 60/238,958, filed on Oct. 9, 2000.

(51) Int. Cl.
*A61B 19/00* (2006.01)

(52) U.S. Cl. ........................................ 128/849; 128/853
(58) Field of Classification Search ........... 128/849–856
See application file for complete search history.

(56) References Cited

U.S. PATENT DOCUMENTS

| | | | | |
|---|---|---|---|---|
| 4,043,328 A | * | 8/1977 | Cawood et al. | 128/850 |
| 4,570,628 A | * | 2/1986 | Neal | 128/853 |
| 4,903,710 A | * | 2/1990 | Jessamine et al. | 128/849 |
| 5,388,593 A | * | 2/1995 | Thomalla | 128/849 |
| 5,419,343 A | * | 5/1995 | Taylor | 128/849 |
| 5,445,165 A | * | 8/1995 | Fenwick | 128/849 |
| 5,979,450 A | * | 11/1999 | Baker et al. | 128/849 |

* cited by examiner

*Primary Examiner* — Michael A. Brown
(74) *Attorney, Agent, or Firm* — Kimberly K. Baxter; Gregory L. Koeller

(57) ABSTRACT

A urological drape is provided defining a vaginal aperture and a finger cot for accessing the rectum of a patient without making contact therewith. The drape includes an adhesive backing for fixing the drape relative to the patient. Preferably, a pouch is provided which is constructed and arranged to catch any fluids which might be discharged from the vagina during an examination or surgical procedure.

20 Claims, 2 Drawing Sheets

PELVIC SURGERY DRAPE

CROSS REFERENCE TO RELATED APPLICATIONS

This application is a continuation of patent application Ser. No. 09/749,254, filed Dec. 27, 2000 now U.S. Pat. No. 7,299,803, now U.S. publication No. 2002/0078964A1 and entitled PELVIC SURGERY DRAPE, which claims priority to U.S. provisional application Ser. No. 60/238,958, filed Oct. 6, 2000, entitled UROLOGICAL DRAPE.

BACKGROUND OF THE INVENTION

The present invention pertains generally to a drape used during urological and gynecological surgical procedures and examinations.

Pelvic reconstructive surgery is a relatively new area of surgery and includes hysterectomies and procedures for correcting such conditions as rectal and vaginal vault prolapse, and vaginal and rectal incontinence. The patients undergoing pelvic floor reconstruction are typically elderly women and often require more than one procedure during surgery. For example, with the increase in the number of vaginal hysterectomies being performed on elderly patients, it has become accepted practice to also perform preventative procedures which ensure vaginal prolapse will not occur following the hysterectomy. Such surgeries have only been performed regularly within the last five years. The earlier work of the inventor in the field of vaginal slings with bone anchors has played a role in the increasing popularity of these procedures. The founding of the Society of Pelvic Reconstructive Surgeons in 1996 also marks the beginning of this area of medicine and played a role in attracting attention to the benefits of combining many of these procedures. The ability to perform multiple pelvic procedures during a single surgery has created a need for devices, such as the drape of the present invention, which increase the speed and efficiency of the surgeon, thereby minimizing the length of the surgery.

During pelvic floor reconstructive surgeries, it is often necessary for a surgeon to conduct repeated digital examinations of a female's vagina and rectum in order to ensure safe and efficient performance of the surgical operation. Moreover, repeated digital and mechanical penetration of the vagina and rectum are necessary to perform the actual procedures (e.g. cutting, suturing and similar tissue manipulation). Such repeated penetrations, however, can increase the likelihood of contamination unless the surgeon is very careful to change surgical gloves between each vaginal and rectal exam. It is not uncommon for a surgeon to use a dozen or more pairs of gloves during pelvic floor reconstructive surgery. Obviously, repeated changing of surgical gloves is time consuming and introduces undesired complications to the surgery.

It is also common in such operations for fluids such as blood and urine to be periodically discharged from the vagina or urethra, especially when the patient is under effects of anesthesia. Such a release of fluids can jeopardize the sterility, and thereby the safety, of the operation.

Finally, notwithstanding the potential negative effects of such fluid discharges, it is desirable to monitor the quantity of such discharges in the event such monitoring will assist the clinician to more easily detect a negative physiological condition of the patient.

In view of the above, it is apparent that there is a need for a medical device which addresses these drawbacks in current surgical techniques. In particular, there is a need for a device that limits the requirement that the attending physician must change gloves between a vaginal and rectal examination, thereby shortening the overall duration of the procedure.

Additionally, there is a need for a device which is capable of catching, retaining and measuring the fluids discharged from the vagina during a surgical procedure.

BRIEF SUMMARY OF THE INVENTION

In a preferred form, the present invention provides a drape for use in a medical setting which meets the needs detailed above as well as other needs not specifically enumerated here. A preferred embodiment uses a flexible sheet having a patient side to be placed against a patient and a surgeon side facing the physician. The sheet defines an opening, fenestration or aperture, of a predetermined size, constructed and arranged to allow access to the patient's vagina or other orifice, with a finger or a probe.

The present invention preferably provides a finger cot, constructed and positioned proximate the opening, which allows a physician's finger to be placed in a second orifice, namely the patient's rectum, such that the cot provides a physical barrier between the rectum and the finger and between the rectum and the vagina.

One aspect of the present invention includes an adhesive backing on the patient side of the flexible sheet, proximate the aperture, which is adherable to the patient.

In another aspect, the present invention provides a drape which includes a pouch, operably attached to the surgeon side of the sheet, capable of containing fluids. Preferably, the pouch is integral with the sheet. More preferably, the pouch comprises graduations such that a quantity of fluid contained in the pouch can be assigned a volumetric value representative of the quantity of fluid. Even more preferably, the pouch includes a stiffening member operably attached to the pouch, holding the pouch open to allow the entry of fluids and preventing the fluids from spilling over the pouch opening.

Another aspect of the present invention provides a drape containing antimicrobial agents operably disposed on the sheet which are capable of reducing the propensity of the drape to become bacterially contaminated. Preferably, the drape further includes antimicrobial agents operably disposed in the adhesive backing which are similarly capable of reducing the propensity of the backing to become bacterially contaminated.

Though the drape of the present invention is designed largely for use during gynecological procedures and various pelvic surgical procedures such as pelvic floor reconstruction, rectal and vaginal prolapse, and hysterectomies, the versatility of the drape lends itself to application during other procedures such as those pertaining to male urology.

These and further aspects, objects and advantages of the present invention will become clearer in light of the following detailed description of illustrative embodiments of this invention described in connection with the drawings.

BRIEF DESCRIPTION OF THE DRAWINGS

The illustrative embodiments may best be described by reference to the accompanying drawings where.

Figure 1:
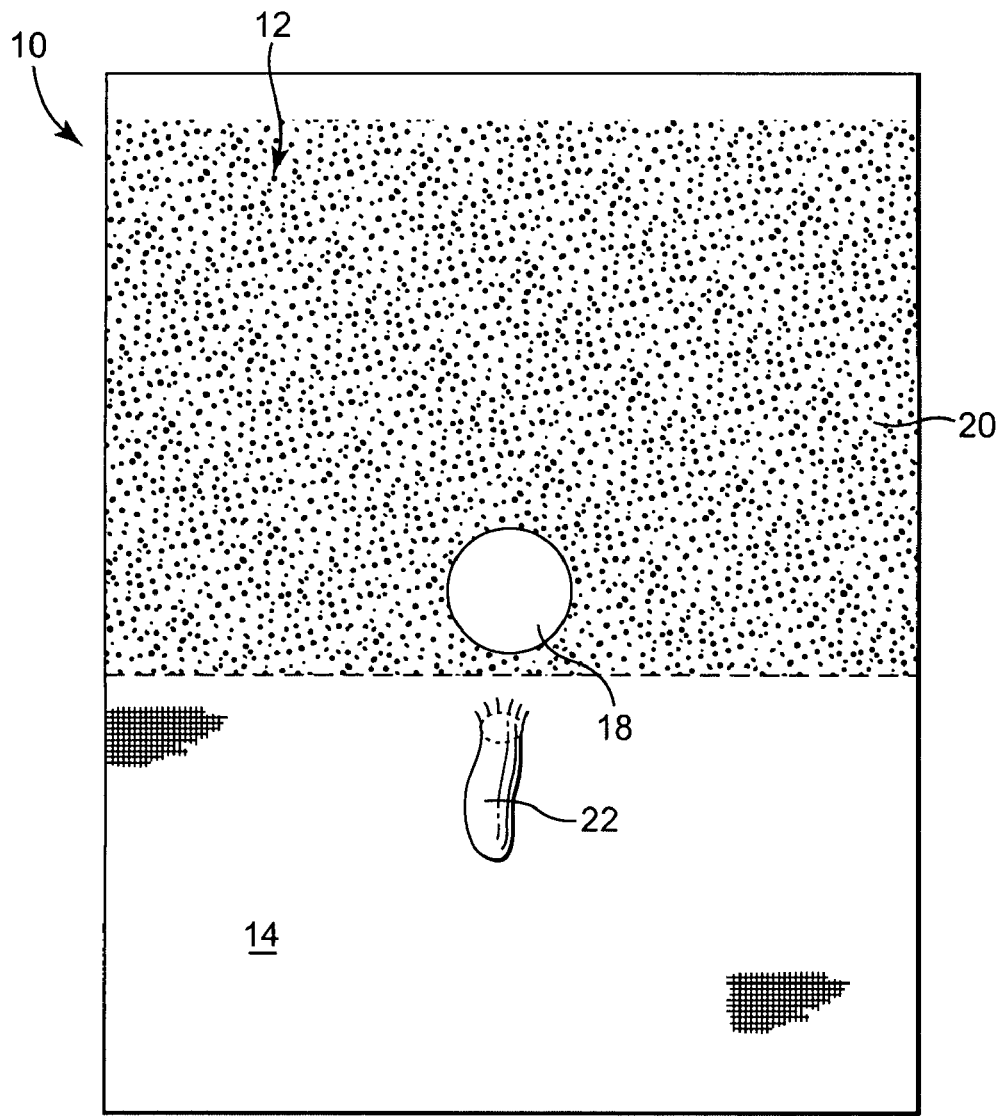
FIG. 1 is a plan view of the patient side of a preferred embodiment of the drape of the present invention.

All figures are drawn for ease of explanation of the basic teachings of the preferred embodiments only. The extensions of the Figures with respect to number, position, relationship, and dimensions of the parts to form the preferred embodiments will be explained or will be within the skill of the art after the following description has been read and understood. Further, the exact dimensional proportions to conform to the specific force, weight, strength, and similar requirements will likewise be within the skill of the art after the following description has been read and understood.

Where used in the various figures of the drawings, the same numerals designate the same or similar parts. Furthermore, any use of the terms "top," "bottom," "upper," "lower," "first," "second," "front," "rear," "end," "edge," "forward," "rearward," "upward," "downward," "inward," "outward," "inside," "side," "horizontal," "vertical," and similar terms, should be understood to have reference only to the structure shown in the drawings as it would appear to a person viewing the drawings and are utilized only to facilitate describing the preferred embodiments.

DETAILED DESCRIPTION OF THE INVENTION

Referring now to the figures, there is shown a medical drape 10 preferably comprising a flexible sheet 12 having a patient side 14 and a surgeon side 16.

Flexible sheet 12 defines a vaginal aperture 18. Vaginal aperture 18 is of a predetermined shape, such as an oval or a circle, and a predetermined size, preferably two to six inches in diameter, more preferably on the order of four inches in length or diameter, and is constructed and arranged to allow a physician to digitally and surgically access a patient's vagina.

A finger cot 22 extends outwardly from the patient side 14 of the sheet 12. The finger cot 22 is constructed and positioned proximate and, preferably below the aperture 18 and is sized to allow a physician to place a finger therein. The finger cot 22 is preferably positioned such that when the aperture 18 is aligned over the vagina of a patient, the finger cot 22 is located near the patient's rectum. In a preferred embodiment, the finger cot 22 is constructed of a thinner, more flexible material, such as butadiene, than that of the sheet 12, and is operably attached thereto. Alternatively, finger cot 22 may be constructed of the same material as the sheet 12 and may be integral therewith.

In a preferred embodiment, a pouch 24 is provided on the surgeon side 16 below the aperture 18 and the finger cot 22. The pouch 24 is operably attached to the surgeon side 16 such that fluids may be contained therein. More preferably, the pouch 24 is integral with the surgeon side 16. It is also preferred that the pouch 24 further includes graduation markings 26. The graduation markings 26 are so positioned that a quantity of fluid contained in the pouch 24 may be assigned a volumetric value representative of the amount of fluid contained in the pouch 24. Preferably, pouch 24 includes a stiffening member 28, operably attached near the top of pouch 24, which is usable to hold the top of the pouch 24 away from the sheet 12, thereby holding the pouch 24 in an open position.

The pouch 24 is, therefore, so positioned below the vaginal aperture 18 such that, in the event that fluids are discharged from the vagina or urethra of the patient, they are caught by the pouch 24 and can be measured using the graduation markings 26. The graduated markings 26 provide a rough estimate of the quantity of fluid present in the pouch 24. However, if a more accurate measurement is desired, a drain port 30, in fluid communication with the pouch, may be provided. The drain port 30 allows a tube to be attached to the bottom of the pouch 24 such that any fluid caught by the pouch 24 is funneled into the tube, through the drain port 30, and may be directed to a rigid, graduated container for accurate measurement.

Figure 3:
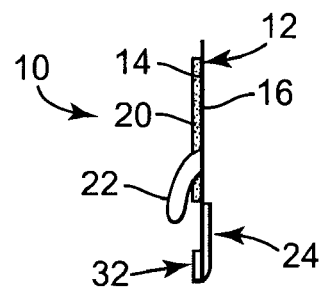
Figure 2:
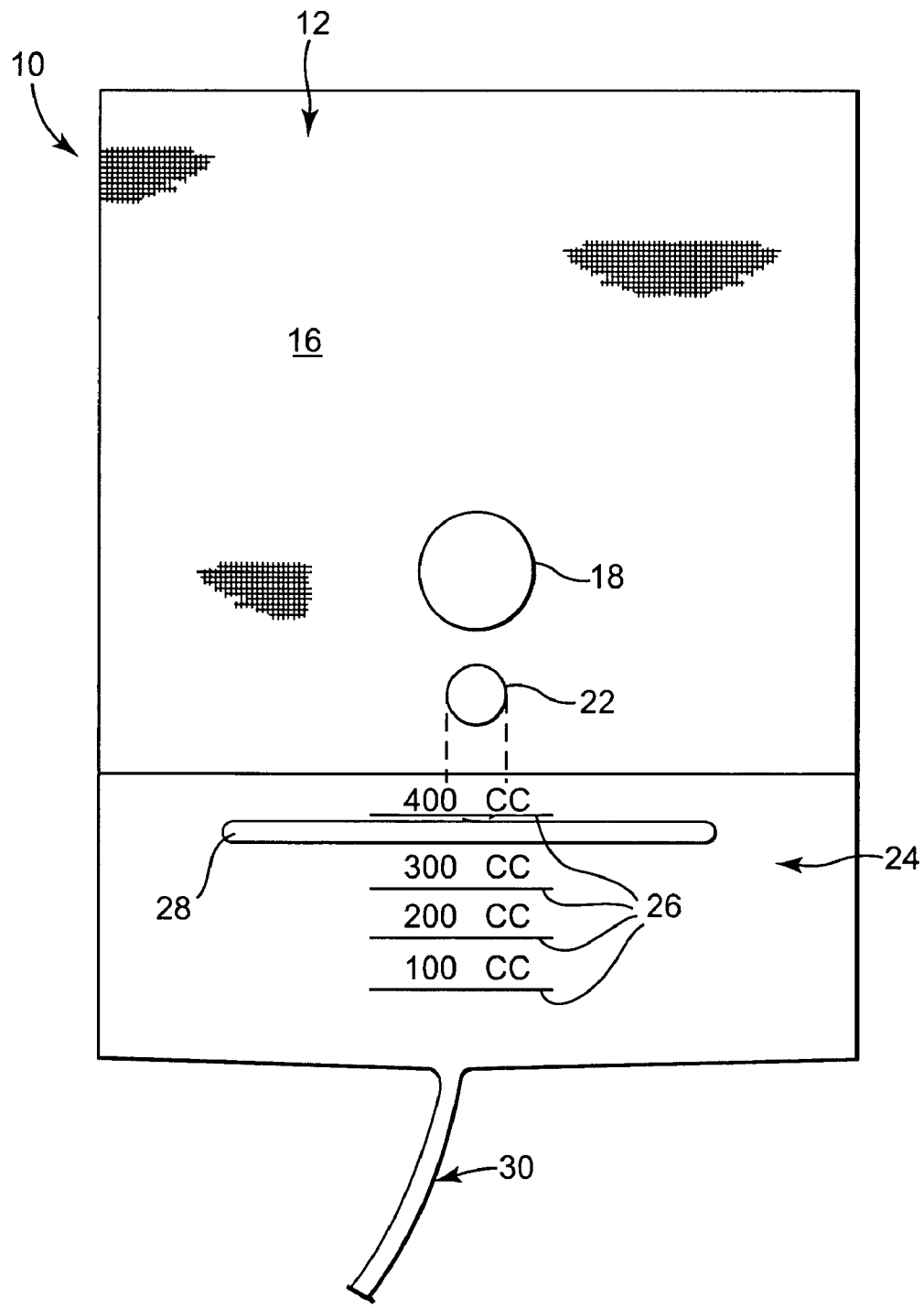
FIG. 2 is a plan view of the surgeon side of a preferred embodiment of the drape of the present invention; and, FIG. 3 is a side elevation of a preferred embodiment of the drape of the present invention.

In order to ensure that drape 10 remains aligned with the patient's vagina, an adhesive backing 20 is preferably provided on the patient side 14 of the sheet 12 proximate aperture 18. More preferably, the adhesive backing 20 surrounds the aperture 18 and is adherable to the patient. Even more preferably, as shown in FIG. 3, the adhesive backing 20 covers that portion of the patient side 14 from about the level of the pouch 24, below the finger cot 22, to nearly the top of the patient side 14, such that maximum adhesion is achieved, thereby virtually eliminating the possibility of the drape 10 becoming misaligned and providing sufficient adhesion to support the weight of a pouch 24 containing fluid, described in more detail below. The adhesive backing 20 further functions to ensure that any fluids discharged from the patient's vagina are directed toward the surgeon side 16 of the sheet 12.

When the drape 10 is used on relatively small patients, adhesive tabs 32, disposed on the patient side 14 of the drape 10 may be used to secure the pouch 24 relative to the patient and, thereby prevent the pouch 24 from interfering with the surgical procedure. The adhesive tabs 32, for instance, may be used to secure the bottom of the drape 10 to other structures such as additional drapes being used during a procedure.

In one preferred embodiment, the sheet 12 includes antimicrobial agents (not shown) capable of reducing a propensity of drape 10 to become bacterially contaminated. It is envisioned that the antimicrobial agents be operably disposed on the sheet 12, on the patient side 14, the surgeon side 16, or both, using any effective method including, but not limited to, impregnation, spray coating, or lamination.

In yet another preferred embodiment, the antimicrobial agents may also be operably disposed in the adhesive backing 20 such that the adhesive backing 20 is capable of reducing a propensity of the adhesive backing 20 to become bacterially contaminated.

In operation, a physician preferably uses the drape 10 during a surgical procedure by placing the drape 10 over the undressed pelvic region such that the patient side 14 faces the patient, and is used to partially cover the patient's pelvic region. The drape 10 is positioned such that the vaginal aperture 18 is aligned with the patient's vagina. In order to ensure adequate adhesion the proximate aperture 18, it may be preferred that the area surrounding the vagina is shaved prior to the application of the drape 10.

The surgeon side 16 is pressed, proximate aperture 18, such that the adhesive 20 adheres to the skin of the patient on the area surrounding her vagina. Care is taken to ensure that the adhesive forms a seal against the patient's skin below the aperture 18 such that in the event that fluids are discharged from the vagina or urethra, they do not leak down the patient side 14 of the sheet 12.

A vaginal examination may then be conducted using the aperture 18 to access the vagina. If it is desired to conduct a subsequent rectal examination, the physician may do so by placing his or her finger into the finger cot 22, and subsequently placing his or her finger and the finger cot 22 into the rectum of the patient. It is not necessary to remove and discard gloves used during the vaginal examination prior to conducting the rectal examination.

Notably, repeated, alternating digital vaginal and rectal examinations may be performed throughout the procedure without changing gloves as a gloved finger or fingers will always be making contact with the vaginal walls, whereas the finger cot 22 will always be making contact with the rectum.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. For example, a similar drape could be used wherein an aperture is used to access the rectum and a finger cot used to access the vagina. Therefore, the scope of the present invention is to be limited only by the included claims.

What is claimed is:

1. A medical drape for examining a patient's vagina and rectum, comprising:
    a flexible sheet having a patient side to be placed against the patient, and a surgeon side facing away from the patient;
    an aperture of a predetermined size on said sheet sized to allow access to the vagina when said sheet is placed on the patient;
    an adhesive backing on said patient side, proximate and surrounding said aperture, wherein the adhesive backing allows the drape to be aligned with the patient's vagina when the adhesive backing is in contact with the patient; and
    a cot disposed on said sheet, said cot sized to allow a finger or probe to be placed in the rectum, wherein said cot provides a barrier between the rectum and the finger or probe.

2. The drape of claim 1 further comprising a pouch attached to said sheet.

3. The drape of claim 2 wherein said pouch is integral with said sheet.

4. The drape of claim 2 wherein said pouch comprises visual graduations according to a volumetric value representative of a quantity of fluid.

5. The drape of claim 2 wherein said pouch includes a stiffening member to hold said pouch away from the surgeon side of said sheet.

6. The drape of claim 1 further comprising at least one antimicrobial agent disposed on said sheet.

7. The drape of claim 6 wherein the at least one antimicrobial agent is disposed in said adhesive backing.

8. The drape of claim 1 wherein said cot is constructed of a material which is more flexible than said sheet.

9. The drape of claim 1 wherein said cot is integral with said sheet.

10. The drape of claim 1 further comprising adhesive tabs, operably disposed on said patient side, displaced from said aperture.

11. The drape of claim 10 wherein said adhesive tabs are located proximate lower corners of said sheet.

12. The drape of claim 2 further comprising a drain port in fluid communication with said pouch, attachable to a tube through which fluid may exit said pouch.

13. The drape of claim 1 wherein said predetermined aperture size is between two and six inches in diameter.

14. The drape of claim 13 wherein said predetermined aperture size is on the order of four inches in diameter.

15. The drape of claim 1 wherein said aperture has an oval shape.

16. A medical drape comprising:
    a sheet of flexible material having an aperture of a predetermined size through which a body orifice may be accessed with a finger or probe;
    an adhesive backing operably disposed on said sheet, proximate and surrounding said aperture, wherein the adhesive backing allows the drape to be aligned with a patient's vagina when the adhesive backing is in contact with the patient;
    a pouch disposed on said sheet to receive fluids discharged from the orifice and,
    a cot disposed on said sheet,
    wherein said cot is sized to enable to access a second body orifice with the finger or probe and wherein said cot provides a barrier between said finger or probe and said second body orifice.

17. The drape of claim 16 further comprising a stiffening member disposed on said pouch.

18. The drape of claim 16 further comprising graduated markings disposed on said pouch according to a volumetric value of fluid retainable in said pouch.

19. The drape of claim 16 wherein said pouch is integral with said sheet.

20. A medical drape comprising:
    a sheet of flexible material having an aperture of a predetermined size through which a body orifice may be accessed with a finger or probe;
    an adhesive backing operably disposed on said sheet, proximate and surrounding said aperture, wherein the adhesive backing allows the drape to be aligned with a patient's vagina when the adhesive backing is in contact with the patient;
    at least one antimicrobial agent disposed in said adhesive backing and,
    a cot disposed on said sheet,
wherein said cot is sized to enable to access a second body orifice with the finger or probe and wherein said cot provides a barrier between said finger or probe and said second body orifice.

* * * * *